US009211376B2

United States Patent
Kouyoumjian et al.

(10) Patent No.: US 9,211,376 B2
(45) Date of Patent: Dec. 15, 2015

(54) INFUSION PUMP DRUG DELIVERY SYSTEM FOR DELIVERING AT LEAST TWO MEDICAMENTS

(75) Inventors: Garen Kouyoumjian, Warwickshire (GB); Malcolm Stanley Boyd, Warwickshire (GB); Daniel Thomas De Sausmarez Lintell, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 224 days.

(21) Appl. No.: 13/885,824

(22) PCT Filed: Nov. 28, 2011

(86) PCT No.: PCT/EP2011/071137
§ 371 (c)(1), (2), (4) Date: May 16, 2013

(87) PCT Pub. No.: WO2012/072561
PCT Pub. Date: Jun. 7, 2012

(65) Prior Publication Data
US 2014/0194815 A1    Jul. 10, 2014

Related U.S. Application Data

(60) Provisional application No. 61/433,809, filed on Jan. 18, 2011.

(30) Foreign Application Priority Data

Nov. 29, 2010   (EP) .................................... 10192994

(51) Int. Cl.
*A61M 1/00*   (2006.01)
*A61M 5/14*   (2006.01)
(Continued)

(52) U.S. Cl.
CPC ........... *A61M 5/1408* (2013.01); *A61M 5/1407* (2013.01); *A61M 5/1409* (2013.01); *A61M 5/14248* (2013.01); *A61M 5/16804* (2013.01); *A61M 5/16827* (2013.01)

(58) Field of Classification Search
CPC ............ A61M 5/1407; A61M 5/1408; A61M 5/1409; A61M 5/14248; A61M 5/14244; A61M 5/16804; A61M 5/16827; A61M 2005/14252; A61M 2005/14256; A61M 2039/1072
USPC ........ 604/48, 82, 89, 93.01, 151, 164.01, 519
See application file for complete search history.

(56) References Cited

U.S. PATENT DOCUMENTS 4,511,352 A    4/1985  Theeuwes et al.
4,596,555 A *  6/1986  Theeuwes ..................... 604/518
(Continued)

OTHER PUBLICATIONS

International Preliminary Report on Patentability for Int. App. No. PCT/EP2011/071137, mailed Jun. 13, 2013.
(Continued)

*Primary Examiner* — Theodore Stigell
*Assistant Examiner* — Tiffany Legette
(74) *Attorney, Agent, or Firm* — McDonnell Boehnen Hulbert & Berghoff LLP

(57) ABSTRACT

The infusion pump drug delivery system and corresponding method disclosed herein allow for continuous delivery of a first fluid and/or medicament from a reservoir operably connected to a pump and selective delivery of a second fluid and/or medicament from a separate reservoir, where the second fluid and/or medicament may be delivered sequentially or simultaneously with the first fluid and/or medicament at the command of the user. Both fluids and/or medicaments are delivered via a single dispense interface.

13 Claims, 12 Drawing Sheets

(51) Int. Cl.
*A61M 5/142* (2006.01)
*A61M 5/168* (2006.01)

(56) References Cited

U.S. PATENT DOCUMENTS 5,776,103 A    7/1998  Kriesel et al.
6,193,704 B1 * 2/2001  Winters .................... 604/500
2010/0160897 A1  6/2010  Ducharme et al.

OTHER PUBLICATIONS

International Search Report and Written Opinion for Int. App. No. PCT/EP2011/071137, completed Feb. 22, 2012.

* cited by examiner

INFUSION PUMP DRUG DELIVERY SYSTEM FOR DELIVERING AT LEAST TWO MEDICAMENTS

CROSS REFERENCE TO RELATED APPLICATIONS

The present application is a U.S. National Phase Application pursuant to 35 U.S.C. §371 of International Application No. PCT/EP2011/071137 filed Nov. 28, 2011, which claims priority to European Patent Application No. 10192994.1 filed Nov. 29, 2010, and U.S. Provisional Patent Application No. 61/433,809 filed Jan. 18, 2011. The entire disclosure contents of these applications are herewith incorporated by reference into the present application.

FIELD OF THE DISCLOSURE

The present application relates to medical systems and methods for delivering at least two medicaments from separate reservoirs (herein, sometimes referred to as "containers," "cartridges," and "packages") to a user. In particular, the present application is concerned with continuous infusion therapy (CIT) pump systems designed to dispense one or more medicaments from respective reservoirs to a user via an infusion set. Each medicament may contain independent (single drug compound) or pre-mixed (co-formulated multiple drug compounds) drug agents.

BACKGROUND

Certain disease states require and/or benefit from treatment using one or more different drug agents (i.e., combination therapy). For example, in some cases it might be beneficial to treat a diabetic with a long-acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus. Although combination therapy may be preferred in some cases, some drug agents need to be delivered in a specific relationship with each other in order to deliver the optimum therapeutic dose. The disclosed system and corresponding method is of particular benefit where combination therapy is desirable, but not possible in a single medicament formulation for reasons such as, but not limited to, stability, compromised therapeutic performance, and toxicology.

There are a number of potential problems associated with the storage and delivery of two active drug agents. For instance, the two active drug agents may interact with each other during long-term storage. Therefore, it is advantageous to store the active drug agents separately and only combine them at the point of delivery via injection, needle-less injection, pumps, or inhalation. However, the process for combining the two active drug agents needs to be simple and convenient for the user to perform reliably, repeatedly, and safely.

A further problem is that the quantities and/or proportions of each active drug agent making up the combination therapy may need to be varied for each user or at different stages of their therapy. For example, certain active drug agents may require a titration period to gradually introduce a user to a "maintenance" dose. A further example would be if one active drug agent requires a non-adjustable fixed dose while the other is varied in response to a user's symptoms or physical condition. This problem means that pre-mixed medicament formulations of multiple active drug agents may not be suitable as these pre-mixed formulations would have a fixed ratio of the active drug agents, which could not be varied by the healthcare professional or user.

Additionally, many users cannot cope with having to use more than one drug delivery system or having to make the necessary accurate calculation of the required dose combination. This is especially true for users with dexterity or computational difficulties. Accordingly, there exists a strong need to provide systems and methods for the delivery of two or more drug agents that is simple for the user to perform.

The disclosed system and corresponding method helps overcome the above-mentioned problems by providing separate reservoirs for the two or more drug agents making up the desired combination therapy. The two or more active drug agents are only combined and/or delivered to the user at delivery. Thus, the two or more active drug agents will not interact with each other during long-term storage. Further, the disclosed system and corresponding method is capable of achieving a wide variety of therapeutic dose profiles, therefore, making combination therapy that may need to be varied for each user or at different stages of their therapy possible.

These and other advantages will become evident from the following more detailed description of the invention.

SUMMARY

Disclosed herein are various examples of an infusion pump drug delivery system and corresponding method for delivering (herein, sometimes referred to as "dispensing") at least two medicaments and/or fluids to a user, where the medicament and/or fluid may contain independent (single compound) or pre-mixed (co-formulated multiple compounds) drug agents. More specifically, the disclosed system and corresponding method allow for continuous delivery of a first medicament from a reservoir operably connected to a pump and selective delivery of a second medicament from a separate reservoir, where the second medicament may be delivered sequentially or simultaneously with the first medicament. Although principally described in this application as an infusion pump drug delivery system, the basic principle could be applicable to other forms of drug delivery, such as, but not limited to, injection pen, inhalation, nasal, ophthalmic, oral, topical, and like systems. In one arrangement, the system may comprise one medicament and a fluid, such as saline or another type of fluid ordinarily used in a drug dispensing system.

By delivering two medicaments from respective reservoirs of a single system, via a single dispense interface the drug delivery system defines a combination therapy (i.e., a therapeutic dose profile between the various drug agents of the medicaments) for a user without the inherent risks associated with using multiple systems and/or multiple needle inputs. This increases patient safety while decreasing the complexity of administering the combination therapy. One or more of the medicaments may be a fluid, defined herein as a liquid, gas or powder that is capable of flowing and that changes shape at a steady rate when acted upon by a force tending to change its shape. Alternatively or additionally, one or more of the medicaments may be a solid, powder, suspension of slurry that may be carried, solubilized or otherwise dispensed with another fluid medicament.

Although Applicants' present patent application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with Applicants' proposed system and method.

As used herein, the term "insulin" shall mean insulin, insulin analogs, insulin derivatives or mixtures thereof, including human insulin or a human insulin analogs or derivatives. Examples of insulin analogs are, without limitation, Gly (A21), Arg(B31), Arg(B32) human insulin; Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala (B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A drug delivery system according to the present disclosure may include (i) a pump operably connected to a first reservoir containing a first medicament, (ii) a delivery tube, wherein an end of the delivery tube is connected to the first reservoir, (iii) a dispense interface in fluid communication with the delivery tube, and (iv) a secondary medicament module in fluid communication with the delivery tube.

The secondary medicament module may comprise a housing, a bypass channel for delivery of the first medicament, a second reservoir containing a second medicament, and an actuation button. The actuation button may be configured to permit delivery of the first medicament when the actuation button is in a non-actuated position and selectively permit delivery of the second medicament when the actuation button is in an actuated position In one exemplary embodiment of the drug delivery system disclosed herein, the system includes (i) a pump operably connected to a first reservoir containing a first medicament, (ii) a delivery tube, wherein an end of the delivery tube is connected to the first reservoir, (iii) a dispense interface in fluid communication with the delivery tube, and (iv) a secondary medicament module in fluid communication with the delivery tube. The secondary medicament module includes (i) a bypass channel for delivery of the first medicament, (ii) a second reservoir containing a second medicament, (iii) a proximal needle, (iv) a distal needle, and (v) an actuation button. The actuation button is configured to permit delivery of the first medicament when the actuation button is in a non-actuated position and selectively permit delivery of the second medicament when the actuation button is in an actuated position. When the actuation button is in the non-actuated position, the proximal and distal needles are in fluid communication with the bypass channel. When the actuation button is in the actuated position, the proximal and distal needles are in fluid communication with the second reservoir.

In another exemplary embodiment of the drug delivery system disclosed herein, the system includes (i) a pump operably connected to a first reservoir containing a first medicament, (ii) a delivery tube, wherein an end of the delivery tube is connected to the first reservoir, (iii) a dispense interface in fluid communication with the delivery tube, and (iv) a secondary medicament module in fluid communication with the delivery tube. The secondary medicament module includes a housing and an actuation button that includes (i) a chamber for a cartridge containing a second medicament and (ii) a bypass channel for delivery of the first medicament. The actuation button is configured to permit delivery of the first medicament when the actuation button is in a non-actuated position and selectively permit delivery of the second medicament when the actuation button is in an actuated position. When the actuation button is in the non-actuated position, the cartridge is laterally offset from the delivery tube, and wherein, when the actuation button is in the actuated position, the cartridge is aligned with the delivery tube. The cartridge may comprise at least one one-way valve that is configured to open when the cartridge is aligned with the delivery tube and the first medicament is pumped through the delivery tube, thereby allowing the second medicament to be delivered.

In another exemplary embodiment of the drug delivery system disclosed herein, the system includes (i) a pump operably connected to a first reservoir containing a first medicament, (ii) a delivery tube, wherein an end of the delivery tube is connected to the first reservoir, (iii) a dispense interface in fluid communication with the delivery tube, and (iv) a secondary medicament module in fluid communication with the delivery tube. The secondary medicament module includes a housing and a rotary member that includes (i) a chamber for a cartridge containing a second medicament and (ii) a bypass channel for delivery of the first medicament. The rotary member is configured to permit delivery of the first medicament when the bypass channel is aligned with the delivery tube and selectively permit delivery of the second medicament when the cartridge is aligned with the delivery tube. When a user desires to deliver the second medicament, the user rotates the rotary member until the cartridge is aligned with the delivery tube. Like the example described above, the cartridge may include at least one one-way valve that is configured to open when the cartridge is aligned with the delivery tube and the first medicament is pumped through the preliminary tube, thereby allowing the second medicament to be delivered.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Various examples of Applicants' drug delivery system and corresponding method are described herein with reference to the following drawings, wherein like numerals denote like entities:

FIG. 5b illustrates the rotary member and cartridge of the secondary medicament module of FIG. 5a;

DETAILED DESCRIPTION

The infusion pump drug delivery system and corresponding method disclosed herein allow for continuous delivery of a first medicament from a reservoir operably connected to a pump and selective delivery of a second medicament from a separate reservoir, where the second medicament may be delivered sequentially or simultaneously with the first medicament at the command of the user. Both medicaments are delivered via a single dispense interface (e.g., a needle). Although the medicaments are referred to herein as being different (i.e., a first and a second medicament), the second medicament need not be different than the first medicament (e.g., an insulin bolus added to basal insulin flow). By activating (e.g., actuating a button operably connected to the reservoir containing the second medicament) a secondary medicament module, the user (or person assisting the user, e.g., a healthcare provider) can select when to deliver the second medicament, which is beneficial where delayed dosing of the second medicament is preferred or required.

As shown in the exemplary embodiments disclosed herein, the second medicament is incorporated into the system's infusion set, which may include a delivery tube, dispense interface, and hub that connects the dispense interface to the delivery tube and that helps maintain the position of the dispense interface on the user's body. To help the dispense interface maintain its position on the user's body, the hub may include or be attached to a disposable patch that includes adhesive for adhering to the user's skin. Where only a single dose is required throughout the limited life of the infusion set, the second medicament may be fully/permanently incorporated (e.g., pre-filled) into the infusion set and thereby can only be dispensed once without replacing the entire infusion set or various components thereof (e.g., the delivery tube and/or secondary medicament module). However, if several doses are required, or the second medicament needs to be varied, the infusion set may feature a port for accepting the introduction of the second medicament or may allow for the replacement of the capsule or cartridge containing the second medicament. Where the infusion set features a port, the port may feature an exclusive attachment means in order to prevent the introduction of inappropriate medicaments.

The majority of exemplary embodiments described herein depict the secondary medicament module near the dispense interface. This helps minimize the impact on the flow of the first medicament and helps avoid flushing of the second medicament during system priming. However, under certain circumstances, these considerations may not be necessary or important and the second medicament may be incorporated further up-stream (i.e., closer to the first medicament reservoir).

Figure 1:
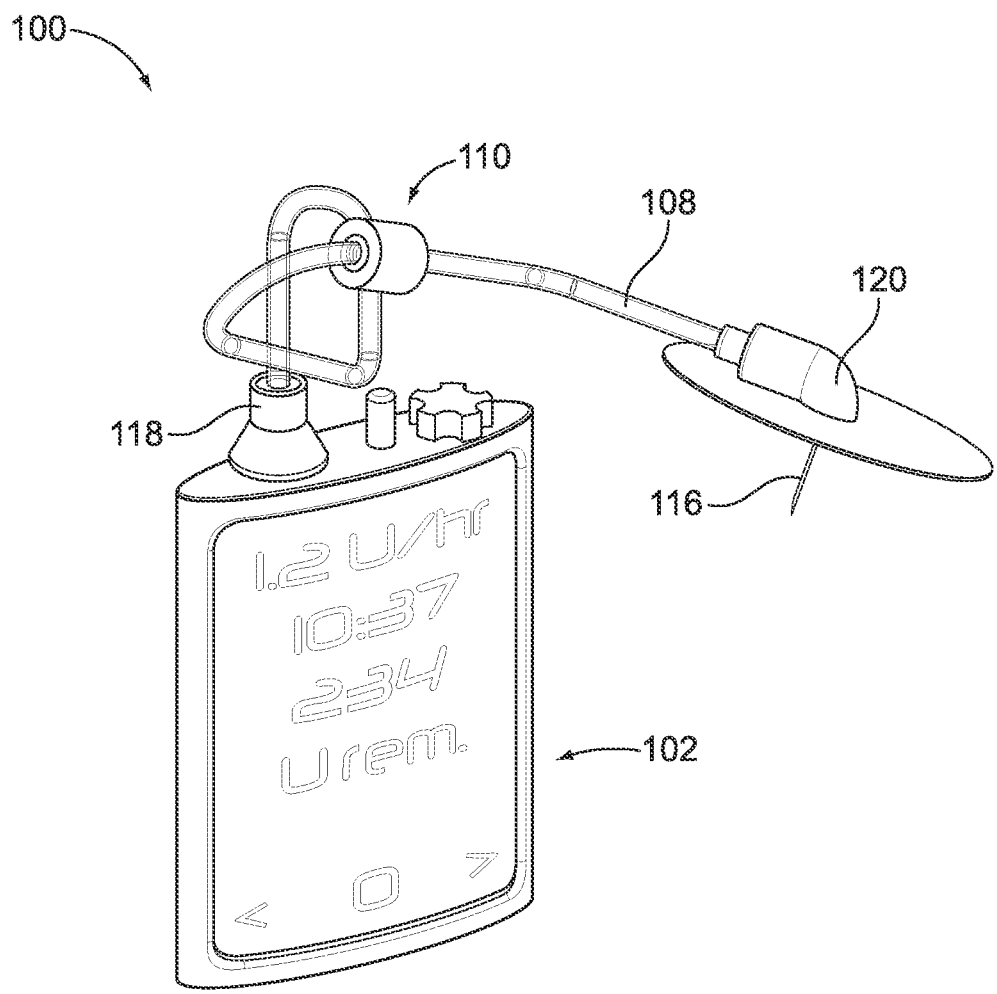
FIG. 1 is a front view of an exemplary infusion pump drug delivery system.
Figure 2:
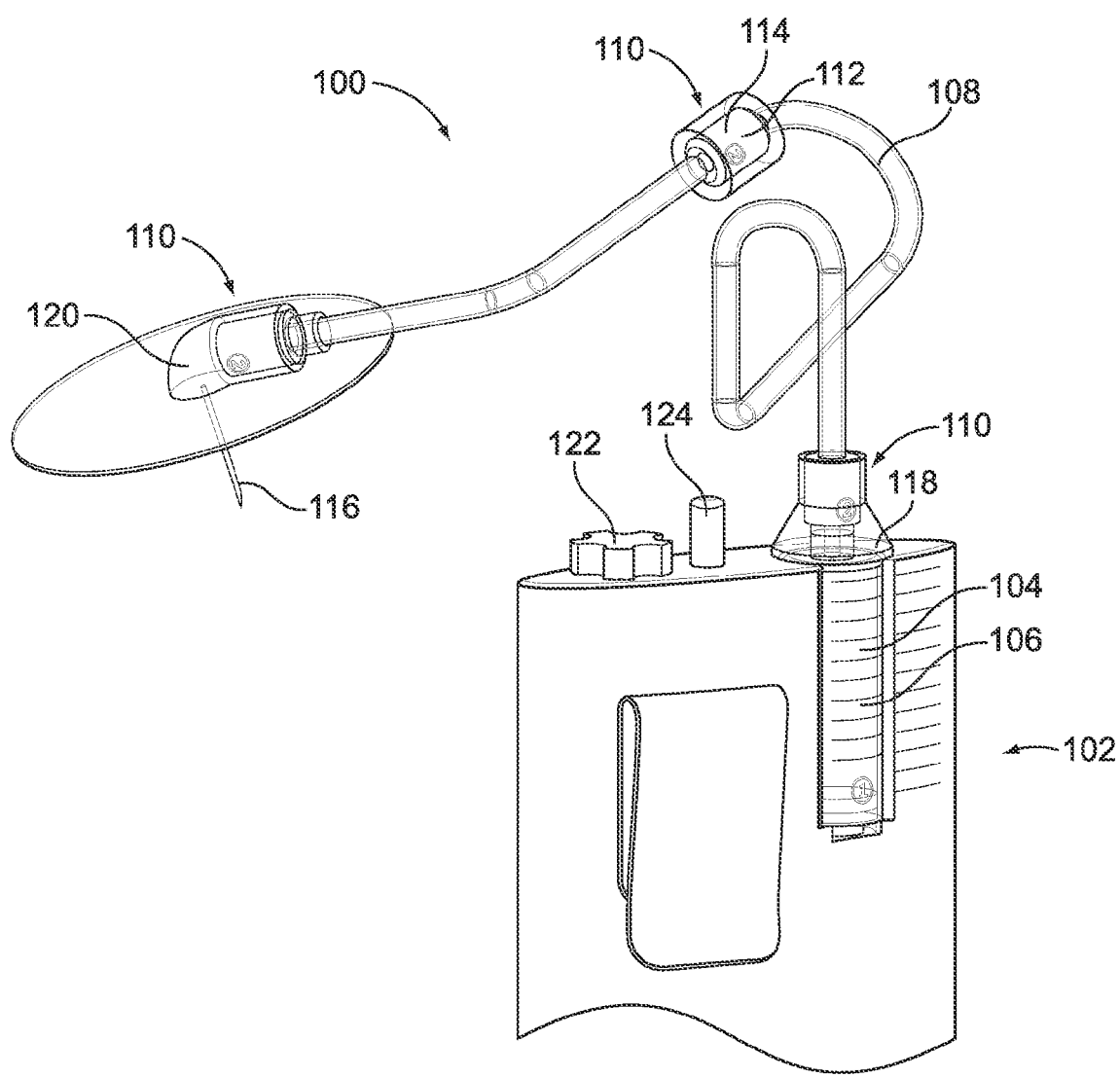
FIG. 2 is a back view of the infusion pump drug delivery system of FIG. 1 and shows various possible locations of the secondary medicament module.

An exemplary infusion pump drug delivery system is shown in FIGS. 1 and 2. As shown, the system 100 generally includes a housing 102 for a pump (not shown) that is operably connected to a first reservoir 104 containing a first medicament 106, a delivery tube 108, a secondary medicament module 110 including a second reservoir 112 containing a second medicament 114, and a dispense interface 116. The secondary medicament module 110 may be located anywhere along the delivery tube 108 between the first reservoir 104 and the dispense interface 116. For example, as shown in FIG. 2, the secondary medicament module 110 may be located (i) within or close to the hub 118 that helps connect the delivery tube 108 to the first reservoir 104, (ii) within or near the hub 120 that helps connect the delivery tube to the dispense interface and that helps maintain the position of the dispense interface on the user's body, and/or (iii) anywhere between (i) and (ii). Although the exemplary embodiments of the system disclosed herein are described as having a single secondary medicament module 110, any number of secondary medicament modules 110 may be used with any of the exemplary systems.

As shown best in FIG. 2, controls 122, 124 (e.g., dose dials, power switches, etc.) are mounted on the outer surface of the housing 102. These controls may power on/off the system 100 and/or may be used to set the desired dose of the first medicament 106. Alternatively, the controls may be provided remotely from the housing 102. For sake of brevity and clarity, additional components such as electronic circuits, controllers, processors, power sources, memory, converters, multiplexers, and the like are not illustrated. However, it should be understood that such components are commonly included in CIT pump systems and are known in the art. Thus, the exemplary embodiments of the system disclosed herein may include such components where appropriate. These components may reside on or in the housing 102 for example.

FIGS. 3*a*-6 illustrate various exemplary embodiments of a secondary medicament module 110 that can be used with FIGS. 1 and 2. Turning to FIGS. 3*a*-*f*, a first exemplary embodiment of a secondary medicament module 310 is shown. The secondary medicament module 310 is located near dispense interface 316 and generally includes a housing 326 (which may be part of hub 320) inside which a slidable capsule 328 is located, a reservoir 312 within the capsule 328 that contains a second medicament 314, a proximal needle 330, a distal needle 332, a bypass channel 336 (see FIG. 3*c*) for delivering a first medicament (not shown), and an actuation button 338.

Figure 3A:
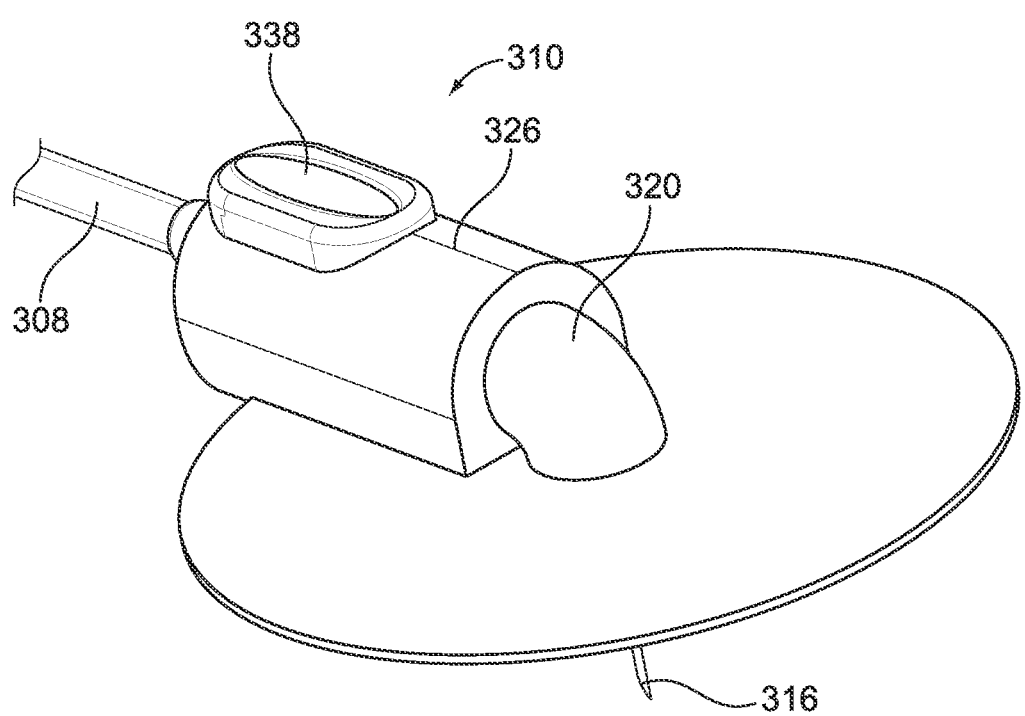
FIG. 3a illustrates an exemplary embodiment of a secondary medicament module that can be used with the system shown in FIGS. 1 and 2.
Figure 3B:
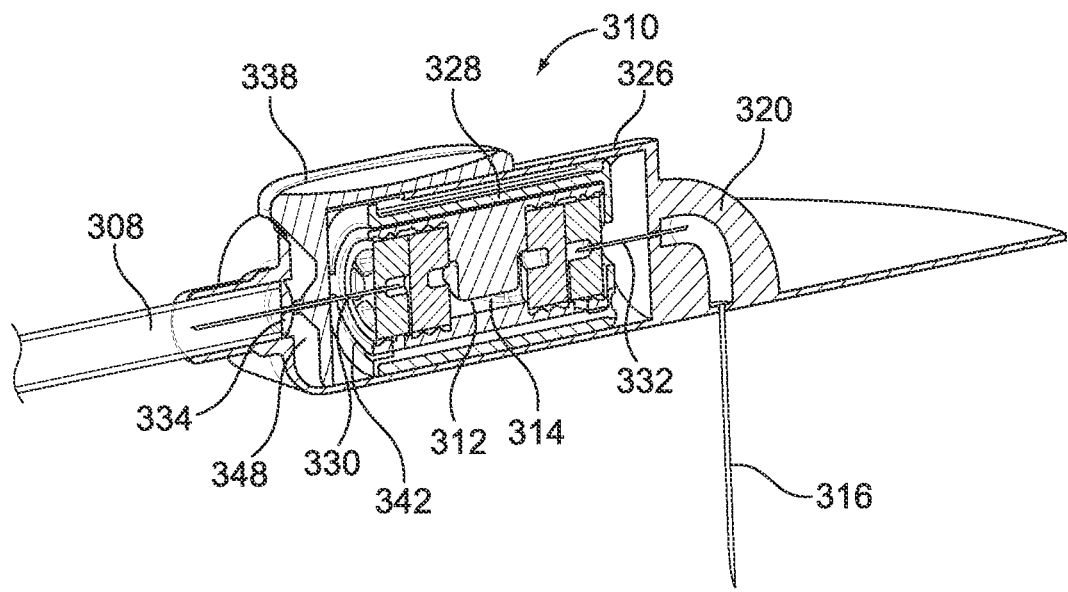
FIG. 3b illustrates a cross-sectional view of the secondary medicament module of FIG. 3a when the button is in its non-actuated position.
Figure 3C:
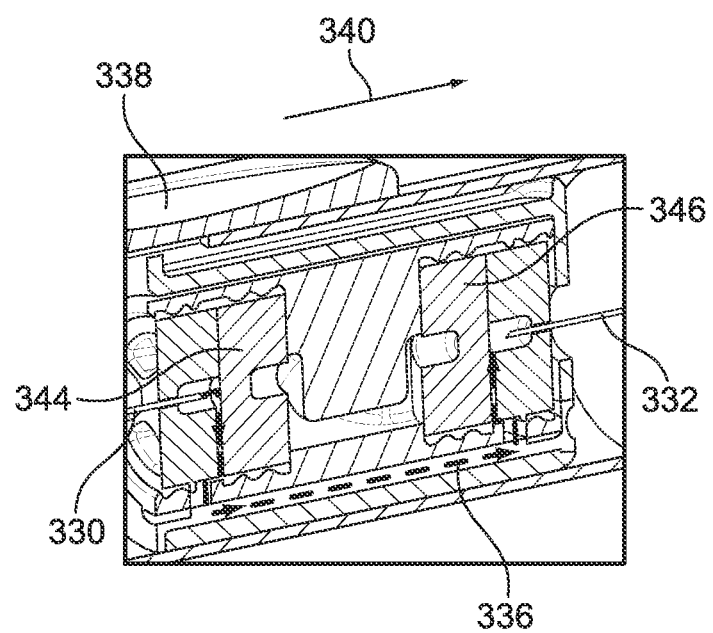
FIG. 3c illustrates another cross-sectional view of the secondary medicament module of FIG. 3a when the button is in its non-actuated position.

When the button 338 is in its non-actuated position (i.e., at its proximal most position, as shown in FIGS. 3*b* and 3*c*), delivery of the first medicament is permitted but delivery of the second medicament 314 is not possible. In this position, the proximal needle 330 provides a fluid conduit from the delivery tube 308 to the bypass channel 336 while the distal needle 332 provides a fluid conduit from the bypass channel 336 to the dispense interface 316. Accordingly, while the pump is running, the first medicament is forced in the distal direction 340 through the delivery tube 308, then through the proximal needle 330, then through the bypass channel 336 (see FIG. 3*c*), then through the distal needle 332, and finally through the dispense interface 316, thereby delivering the first medicament to the user.

When the user desires to deliver the second medicament 314, the user activates the secondary medicament module 310 by sliding the actuation button 338 in the distal direction 340 until the button 338 reaches its actuated position (i.e., when the proximal and distal needles 330, 332 are both in fluid communication with the reservoir 312 containing the second medicament 314). As the user slides the button 338 in the distal direction 340 the proximal needle 330 correspondingly moves in the distal direction 340 because the proximal needle 330 is fixed to the button 338 (perhaps by adhesive). Alternately, the proximal needle 330 may be mechanically trapped or bonded through co-molding. A sliding septum or seal 334 located between the delivery tube 308 and the capsule 328 helps guide the proximal needle 330 as it moves in the distal direction 340 while preventing the first medicament from leaking into the cavity 342 of the housing 326. The sliding seal 334 may be fixed to, or part of, the distal end of the delivery tube 308 or the housing 326 of the secondary medicament module 310.

Figure 3D:
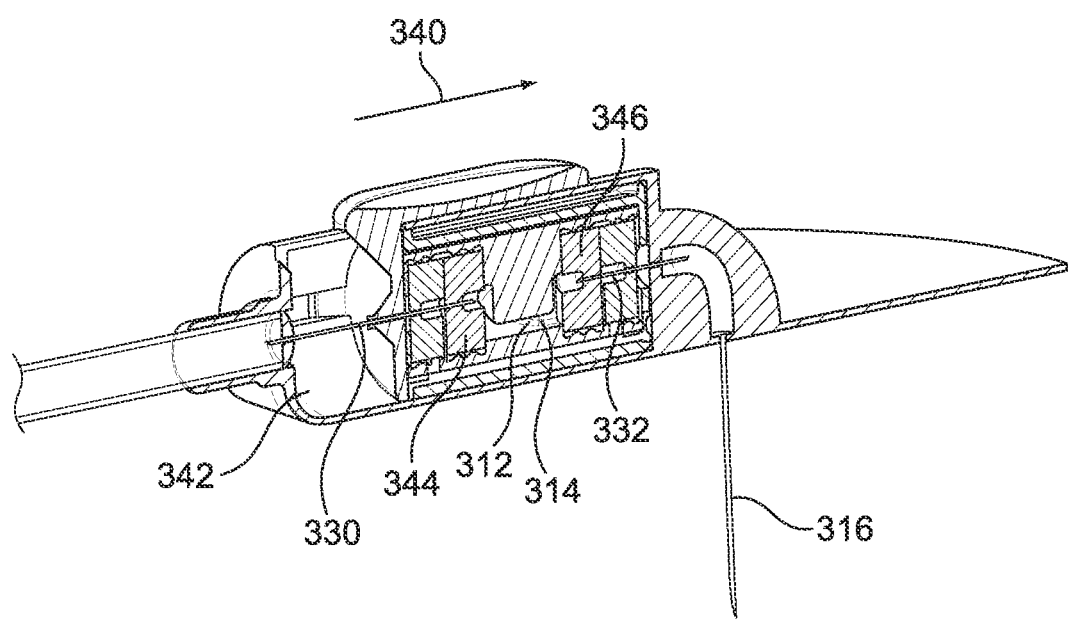
FIG. 3d illustrates another cross-sectional view of the secondary medicament module of FIG. 3a when the button is in its actuated position.

As the user slides the button 338 in the distal direction 340, the distal end of the proximal needle 330 pierces the proximal seal 344 of the reservoir 312 at a first predetermined axial position of the button 338, thereby placing the proximal needle 330 in fluid communication with the reservoir 312 containing the second medicament 314. At a second predetermined axial position of the button 338, the internal portion 348 of the button 338 comes into abutment with the capsule 328, thus, further distal movement 340 of the button 338 causes corresponding movement of the slidable capsule 228. At a third predetermined axial position of the button 338, the proximal end of the distal needle 332 (which is fixed to the housing 326) pierces the distal seal 346 of the reservoir 312, thus placing the distal needle 332 in fluid communication with the reservoir 312 containing the second medicament 314. After both the proximal and distal needles 330, 332 are in fluid communication with the reservoir 312, the button 338 is in its actuated position (as shown in FIG. 3*d*). Although described herein as the first, second, and third predetermined axial positions of the button 338, the first and second predetermined axial positions may be the same. In other words, the distal end of the proximal needle 330 may pierce the proximal seal 344 of the reservoir 312 at substantially the same time that the internal portion 348 of the button 338 comes into abutment with the capsule 328.

After both needles 330, 332 are in fluid communication with the reservoir 312, the distally directed force of the first medicament, which is generated by the pump, forces the second medicament 314 out of the reservoir 312, through the distal needle 330, and through the dispense interface 316, thereby delivering the second medicament 314 to the user. The secondary medicament module 310 may be configured such that, when the button 338 is in its actuated position, the distal and proximal ends of the proximal and distal needles 330, 332 respectively are very close to the proximal and distal seals 344, 346 respectively, thus minimizing the amount of dead space inside the reservoir 312. After the second medicament 314 is delivered to the user, the first medicament will continue to be delivered to the user (via the flow path created by the reservoir 312 being in fluid communication with both needles 330, 332) as long as the pump continues to pump first medicament from its reservoir.

Figure 3E:
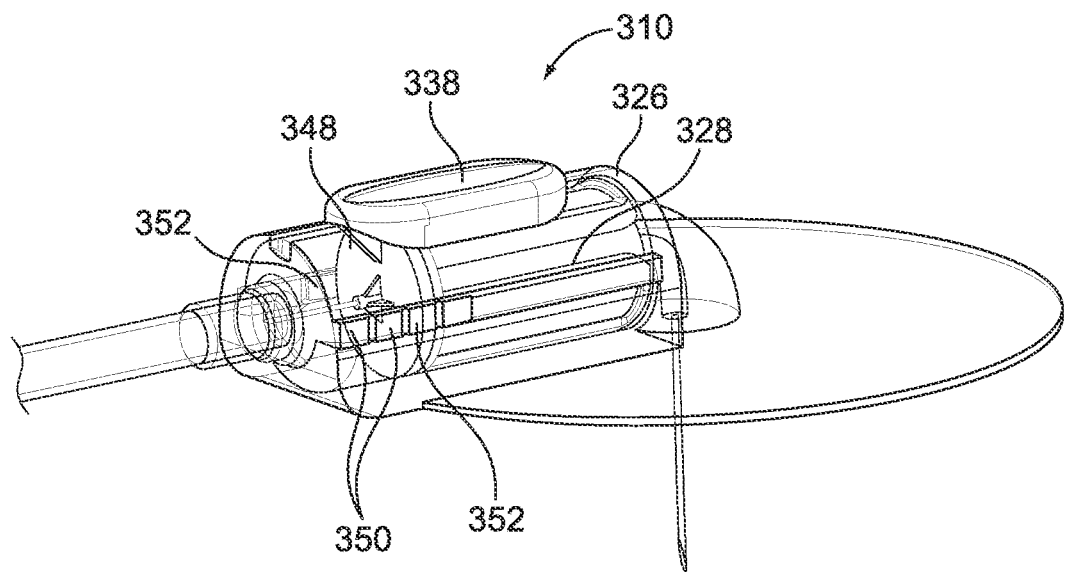
FIG. 3e illustrates a partially transparent view of the secondary medicament module of FIG. 3a when the button is in its actuated position.
Figure 3F:
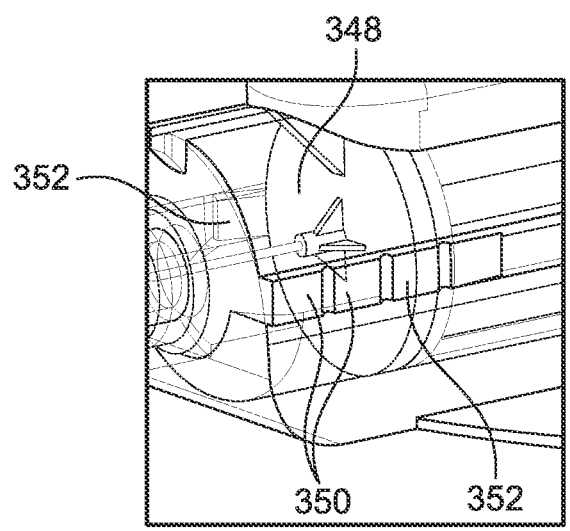
FIG. 3f illustrates another partially transparent view of the secondary medicament module of FIG. 3a when the button is in its actuated position.

As shown in FIGS. 3*e* and 3*f*, the housing 326 of the secondary medicament module 310 may be provided with grooves 350 that are configured to engage snap arms 352 of the button 338, thus providing tactile and/or audible feedback to the user. As shown, the housing 326 may be provided with two rows of three grooves 350 that are configured to engage two snap arms 352 of the button 338, where the rows are disposed opposite to one another on the inner surface of the housing 326 and the snap arms 352 are disposed opposite each other on the outer edge of the portion 348 of the button 338 that interfaces with the capsule 328. Each groove 350 may correspond with one of the predetermined axial positions of the button 338 described above. For instance, the proximal most groove 350 may correspond to the first predetermined axial position of the button 338, the middle groove 350 may correspond to the second predetermined axial position of the button 338, and the distal most groove 350 may correspond to the third predetermined axial position of the button 338. Any number of grooves 350 and snap arms 352 may be used. Regardless of the number of grooves 350 and snap arms 352, it is desirable to provide a groove 350 that corresponds to the actuated position of the button 338 so that the user knows when the button 338 is in its actuated position and thus when the second medicament 314 will be delivered.

The grooves 350 and corresponding snap arms 352 may be configured to prevent the button 338 from being reversed to its non-actuated position after reaching its actuated position, thus making the secondary medicament module 310 disposable (i.e., single use). This may be accomplished using a one-way ratchet-type system. Accordingly, after delivery of the second medicament 314, the secondary medicament module 310 and/or entire infusion set would need to be replaced in order to deliver a second dose of the same or different second medicament. Alternatively, the secondary medicament module 310 may be reusable (i.e., multi-use). As such, the button 338 may be configured to be reversed to its non-actuated position. Further, the secondary medicament module 310 may be provided with a port for (i) receiving a refill dose of a second medicament and (ii) transferring the refill dose to the reservoir 312. In another reusable embodiment, the secondary medicament module 310 may be configured such that the entire capsule 328 can be replaced.

Figure 4A:
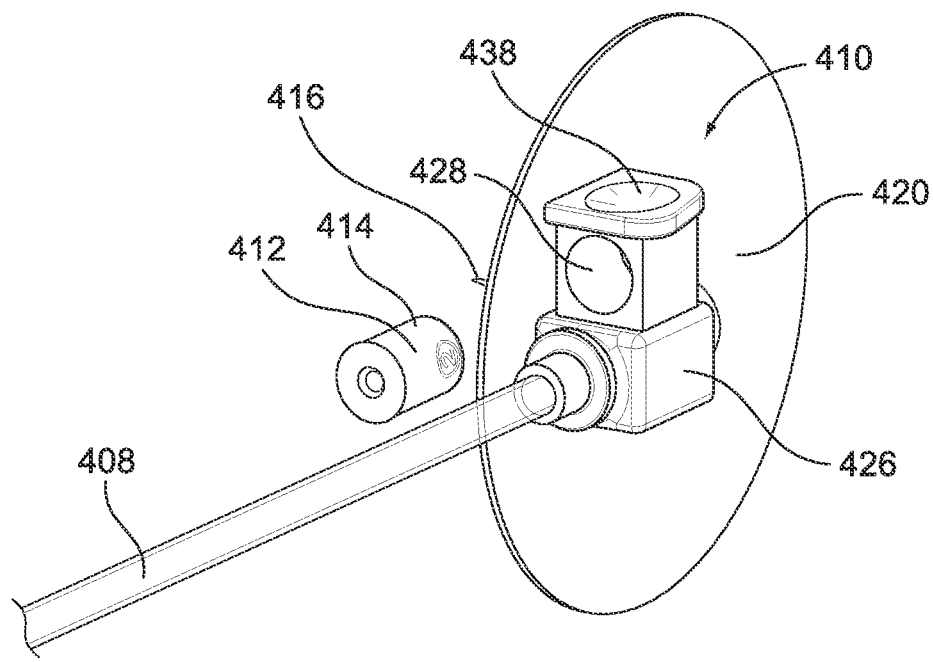
FIG. 4a illustrates a partially exploded view of another exemplary embodiment of a secondary medicament module that can be used with the infusion pump drug delivery system shown in FIGS. 1 and 2.
Figure 4B:
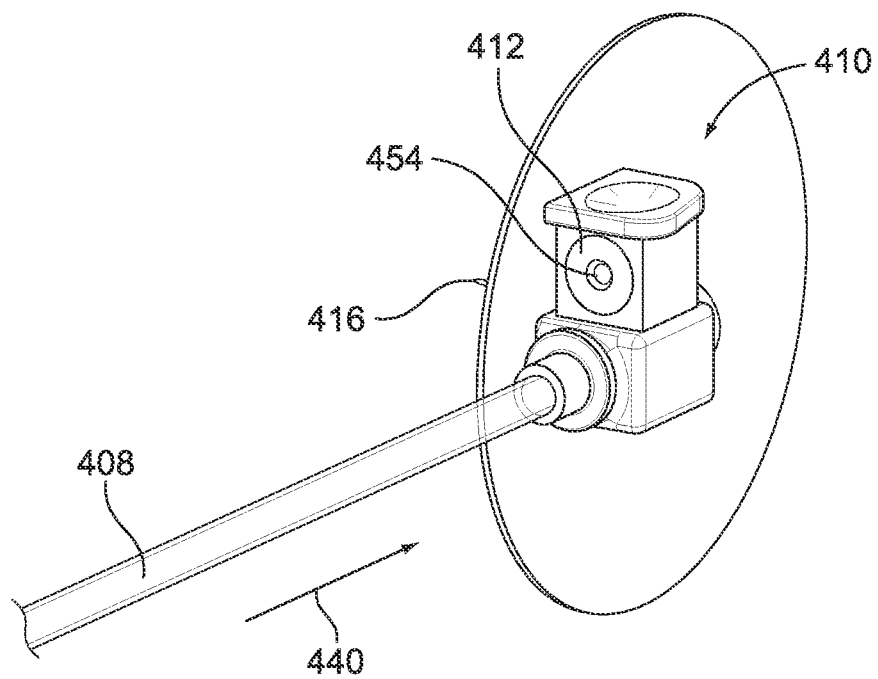
FIG. 4b illustrates the secondary medicament module of FIG. 4a when the button is in its non-actuated position.
Figure 4C:
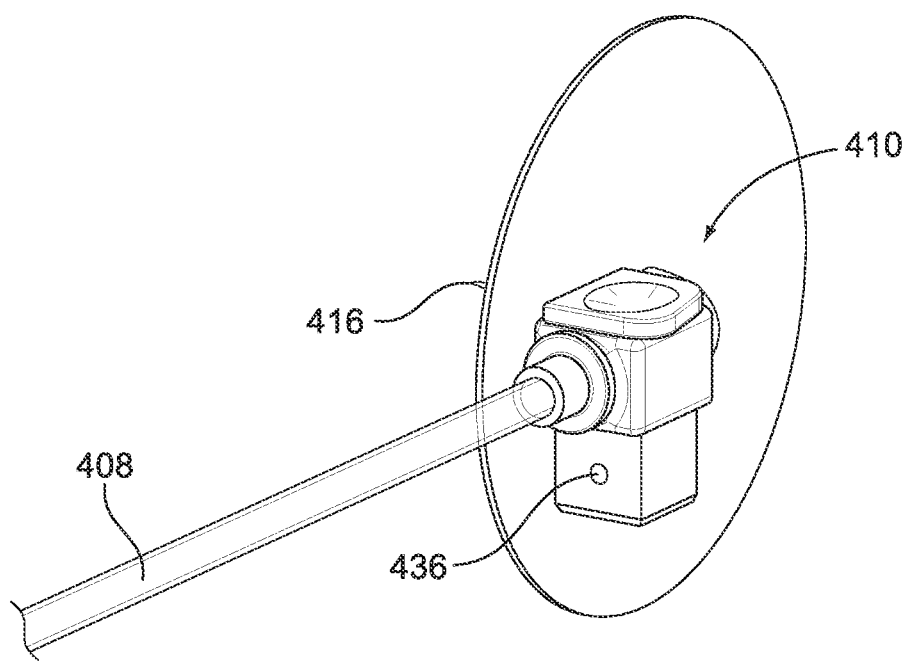
FIG. 4c illustrates the secondary medicament module of FIG. 4a when the button is in its actuated position.

FIGS. 4a-c illustrate another exemplary embodiment of a secondary medicament module 410. As shown, the secondary medicament module 410 is located near dispense interface 416 and generally includes a housing 426 (which may be part of hub 420) and an actuation button 438 that includes (i) a chamber 428 for holding a cartridge 412 that contains a second medicament 414 and (ii) a bypass channel 436 (see FIG. 4c). The secondary medicament module 410 may be disposable (i.e., single use) or reusable (i.e., multiuse). If the secondary medicament module 410 is disposable, it may be provided with a pre-installed permanent cartridge 412. If the secondary medicament module 410 is reusable, then the user may have to install the cartridge 412 into the chamber 428 when the user desires to deliver a second medicament dose. In such a case, it is important to maintain sterility of the cartridge 412 and the second medicament 414 contained therein and to prevent leakage of the second medicament 414 prior to activating the secondary medicament module 410. Thus, the cartridge 412 may be provided with seals (not shown) that cover its proximal and distal ends. These seals may be foil seals that can be removed by the user prior to activating the secondary medicament module 410. Further, the chamber 428 may feature an exclusive attachment means that only accepts certain cartridges, which prevents the introduction of inappropriate medicaments.

When the secondary medicament module 410 is in its non-actuated position (i.e., when the bypass channel 436 is in fluid communication with the delivery tube 408 and the dispense interface 416, and when the cartridge 412 is laterally offset from the delivery tube 408, as shown best in FIG. 4b), delivery of the first medicament is permitted but delivery of the second medicament 414 is prohibited. In this position, the bypass channel 436 provides a fluid conduit from the delivery tube 408 to the dispense interface 416. Accordingly, while the pump is running, the first medicament is forced in the distal direction 440 through the delivery tube 408, then through the bypass channel 436, and finally through the dispense interface 416, thereby delivering the first medicament to the user.

When the user desires to deliver the second medicament 414, the user activates the secondary medicament module 410 by depressing the button 438 until it reaches its actuated position (i.e., when the cartridge 412 is aligned with the delivery tube 408 such that the cartridge channel 454 is in fluid communication with the delivery tube 408 and the dispense interface 416, as shown in FIG. 3c). Although not shown, both the proximal and distal ends of the cartridge channel 454 are provided with one-way flow valves that are designed to open under the force of the first medicament when it is being pumped from its reservoir. Thus, once the cartridge 412 is aligned with the delivery tube 408 such that the cartridge channel 454 is in fluid communication with the delivery tube 408 and the dispense interface 416, the force of the first medicament causes the one-way valves to open. Once the valves are open, the first medicament forces the second medicament 414 out of the cartridge 412 and through the dispense interface 416, thereby delivering the second medicament 414 to the user. After the second medicament 414 is delivered to the user, the first medicament will continue to be delivered to the user (via the flow path created by the cartridge channel 454 being in fluid communication with the delivery tube 408 and the dispense interface 416) as long as the pump continues to pump first medicament from its reservoir.

Although not shown, the housing of the secondary medicament module 410 may be provided with grooves 450 that are configured to engage snap arms 452 of the button 438, thus providing tactile and/or audible feedback to the user. Any number of grooves 450 and snap arms 452 may be used. Regardless of the number of grooves 450 and snap arms 452, it is desirable to provide a groove 450 that corresponds to the actuated position of the button 438 so that the user knows when the button 438 is in its actuated position and thus when the second medicament 414 will be delivered.

The grooves 450 and corresponding snap arms 452 may be configured to prevent the button 438 from being reversed to its non-actuated position after reaching its actuated position, thus making the secondary medicament module 410 disposable (i.e., single use). This may be accomplished using a one-way ratchet-type system. Accordingly, after delivery of the second medicament 414, the secondary medicament module 410 and/or entire infusion set would need to be replaced in order to deliver a second dose of the same or different second medicament. Alternatively, as noted above, the secondary medicament module 410 may be reusable. As such, the button 438 may be configured to be reversed to its non-actuated position. Once the button 438 is in its non-actuated position, the used cartridge may be replaced with new one.

FIGS. 5a-f illustrate another exemplary embodiment of a secondary medicament module 510. As shown, the secondary medicament module 510 is located near dispense interface 516 and generally includes a housing 526 (which may be part of hub 520) and a rotary actuation member 538 that includes (i) a chamber 528 for holding a cartridge 512 that contains a second medicament 514 and (ii) a bypass channel 536 (see FIG. 5b) for delivering a first medicament from a reservoir operably connected to a pump. The secondary medicament module 510 may be disposable (i.e., single use) or reusable (i.e., multiuse). If the secondary medicament module 510 is disposable, it may be provided with a pre-installed permanent cartridge 512. If the secondary medicament module 510 is reusable, then the user may have to install the cartridge 512 into the chamber 528 when the user desires to deliver a second medicament dose. In such a case, it is important to maintain sterility of the cartridge 512 and the second medicament 514 contained therein and to prevent leakage of the second medicament 514 prior to activating the secondary medicament module 510. Thus, the cartridge 512 may be provided with seals (not shown) that cover its proximal and distal ends. These seals may be foil seals that can be removed by the user prior to activating the secondary medicament module 510. Further, the chamber 528 may feature an exclusive attachment means that only accepts certain cartridges, which prevents the introduction of inappropriate medicaments.

Figure 5A:
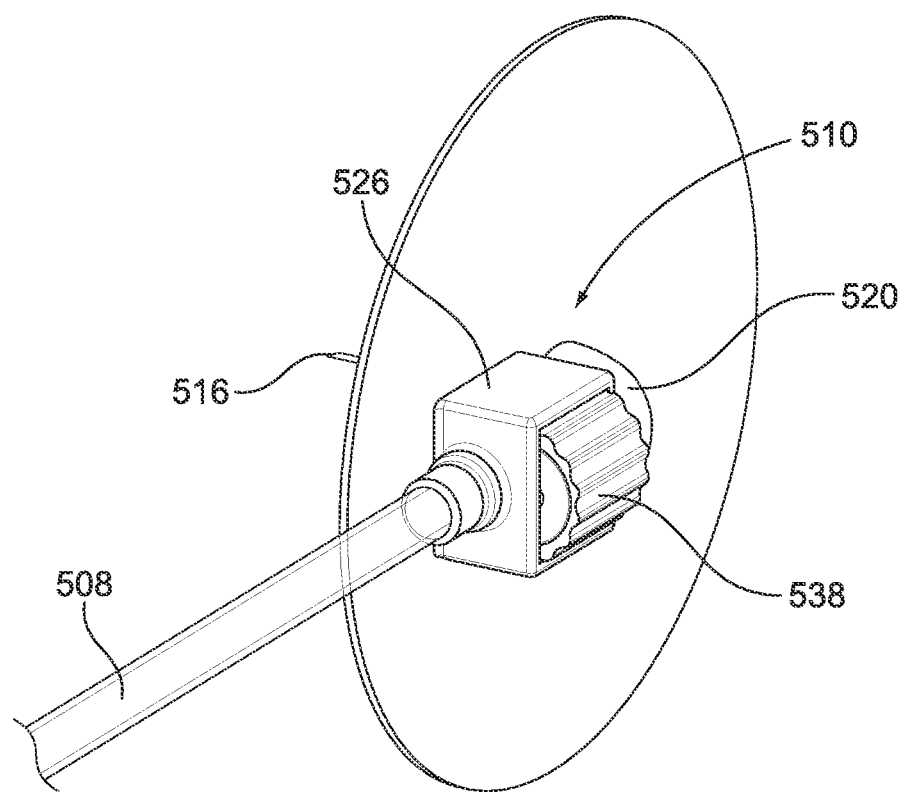
FIG. 5a illustrates another exemplary embodiment of a secondary medicament module that can be used with the infusion pump drug delivery system shown in FIGS. 1 and 2.
Figure 5B:
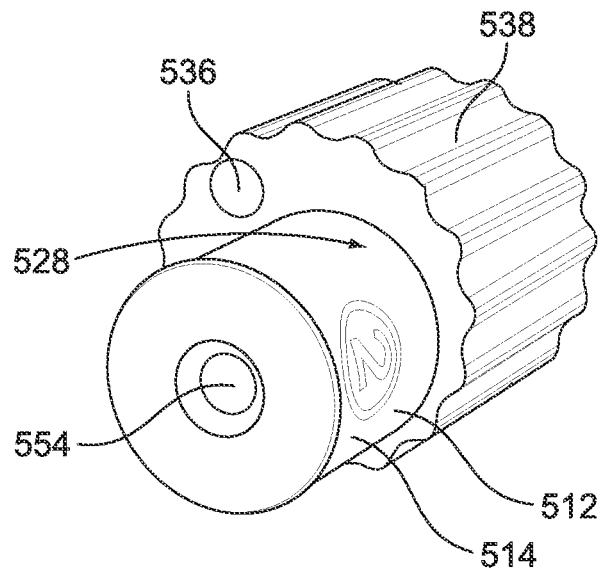
Figure 5C:
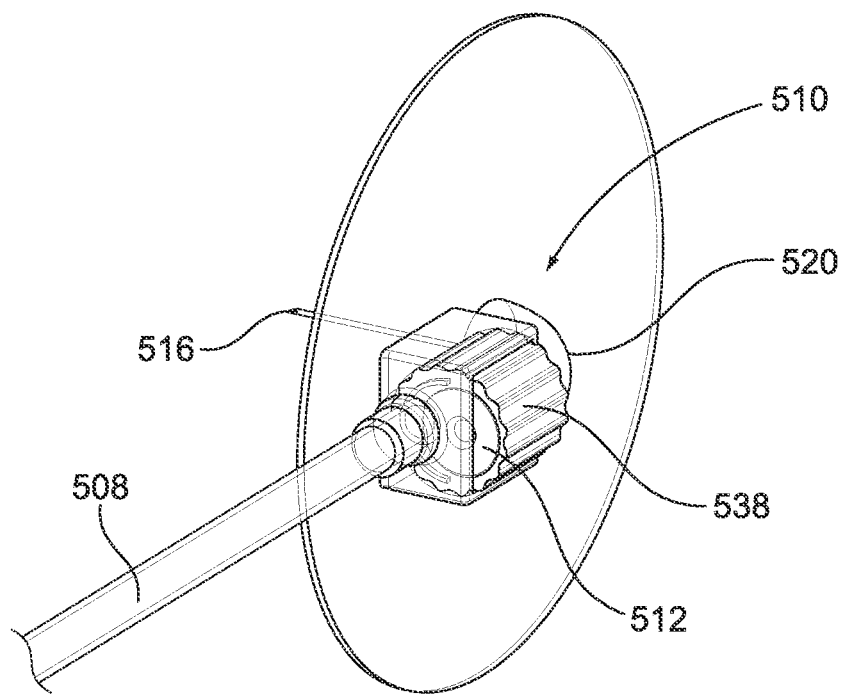
FIG. 5c illustrates a partially transparent view of the secondary medicament module of FIG. 5a when the rotary member is in its non-actuated position.

When the secondary medicament module 510 is in its non-actuated position (i.e., when the bypass channel 536 is in fluid communication with the delivery tube 508 and the dispense interface 516, and when the cartridge 512 is laterally offset from the delivery tube 508, as shown in FIGS. 5a and 5c), delivery of the first medicament is permitted but delivery of the second medicament 514 is prohibited. In this position, the bypass channel 536 provides a fluid conduit from the delivery tube 508 to the dispense interface 516. Accordingly, while the pump is running, the first medicament is forced in the distal direction 540 through the delivery tube 508, then through the bypass channel 536, and finally through the dispense interface 516, thereby delivering the first medicament to the user.

Figure 5D:
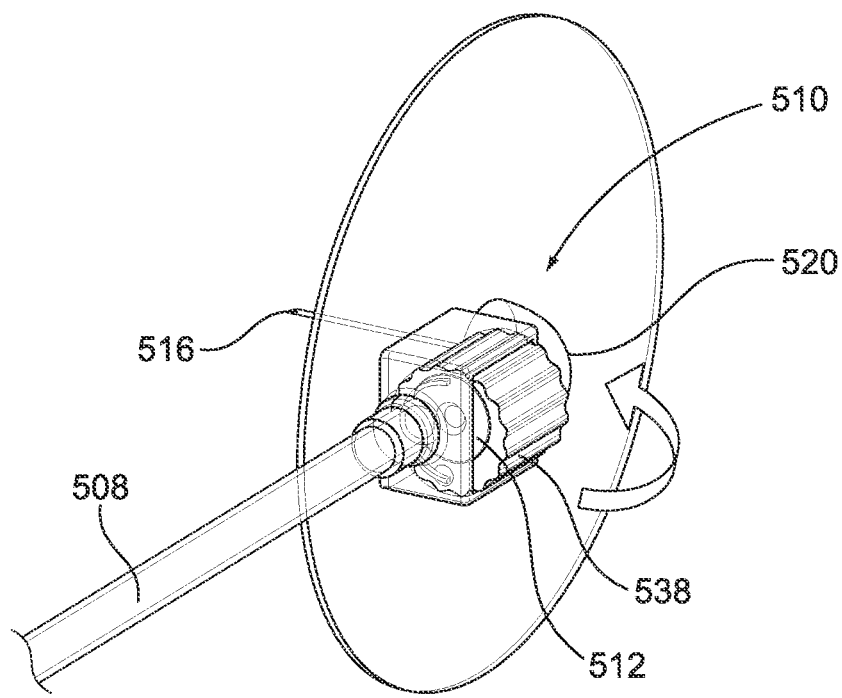
FIG. 5d illustrates a partially transparent view of the secondary medicament module of FIG. 5a when the rotary member is being rotated.
Figure 5E:
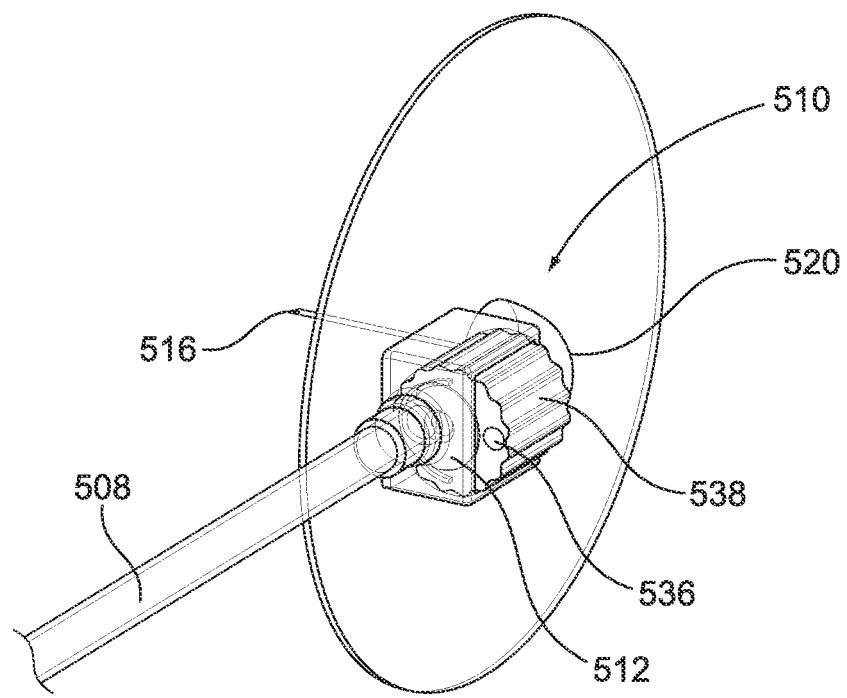
FIG. 5e illustrates a partially transparent view of the secondary medicament module of FIG. 5a when the rotary member is in its actuated position.
Figure 5F:
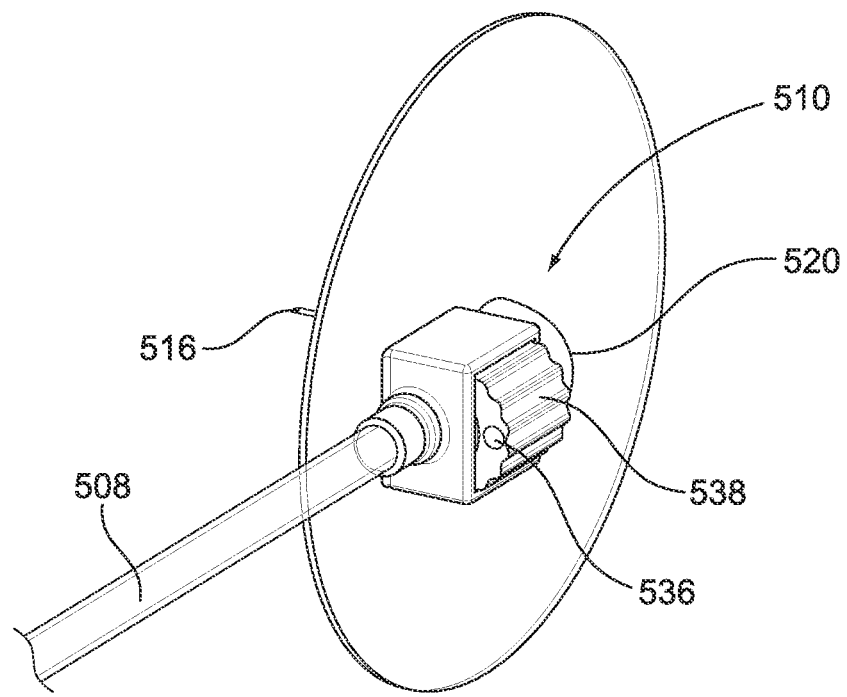
FIG. 5f illustrates the secondary medicament module of FIG. 5a when the rotary member is in its actuated position.

When the user desires to deliver the second medicament 514, the user activates the secondary medicament module 510 by rotating the rotary member 538 (FIG. 5d shows the rotary member 538 during rotation from its non-actuated position to its actuated position) until it reaches its actuated position (i.e., when the cartridge 512 is aligned with the delivery tube 508 such that the cartridge channel 554 is in fluid communication with the delivery tube 508 and the dispense interface 516, as shown in FIGS. 5e and 5f). Although not shown, both the proximal and distal ends of the cartridge channel 554 are provided with one-way flow valves that are designed to open under the force of the first medicament when it is being pumped from its reservoir. Thus, once the cartridge 512 is aligned with the delivery tube 508 such that the cartridge channel 554 is in fluid communication with the delivery tube 508 and the dispense interface 516, the force of the first medicament causes the one-way valves to open. Once the valves are open, the first medicament forces the second medicament 514 out of the cartridge 512 and through the dispense interface 516, thereby delivering the second medicament 514 to the user. After the second medicament 514 is delivered to the user, the first medicament will continue to be delivered to the user (via the flow path created by the cartridge channel 554 being in fluid communication with the delivery tube 508 and the dispense interface 516) as long as the pump continues to pump first medicament from its reservoir.

The housing 526 of the secondary medicament module 510 may be provided with grooves 550 that are configured to engage snap arms 552 of the rotary member 538, thus providing tactile and/or audible feedback to the user. Any number of grooves 550 and snap arms 552 may be used. Regardless of the number of grooves 550 and snap arms 552, it is desirable to provide a groove 550 that corresponds to the actuated position of the rotary member 538 so that the user knows when the button 538 is in its actuated position and thus when the second medicament 514 will be delivered.

The grooves 550 and corresponding snap arms 552 may be configured to prevent the rotary member 538 from being reversed to its non-actuated position after reaching its actuated position, thus making the secondary medicament module 510 disposable (i.e., single use). This may be accomplished using a one-way ratchet-type system. Accordingly, after delivery of the second medicament 514, the secondary medicament module 510 and/or entire infusion set would need to be replaced in order to delivery a second dose of the same or different second medicament. Alternatively, as noted above, the secondary medicament module 510 may be reusable. As such, the rotary member 538 may be configured to be reversed to its non-actuated position. Once the rotary member 538 is in its non-actuated position, the used cartridge 512 may be replaced with a new one. In order to replace the cartridge, the rotary member 538 may need to be removed from the housing 526.

Figure 6:
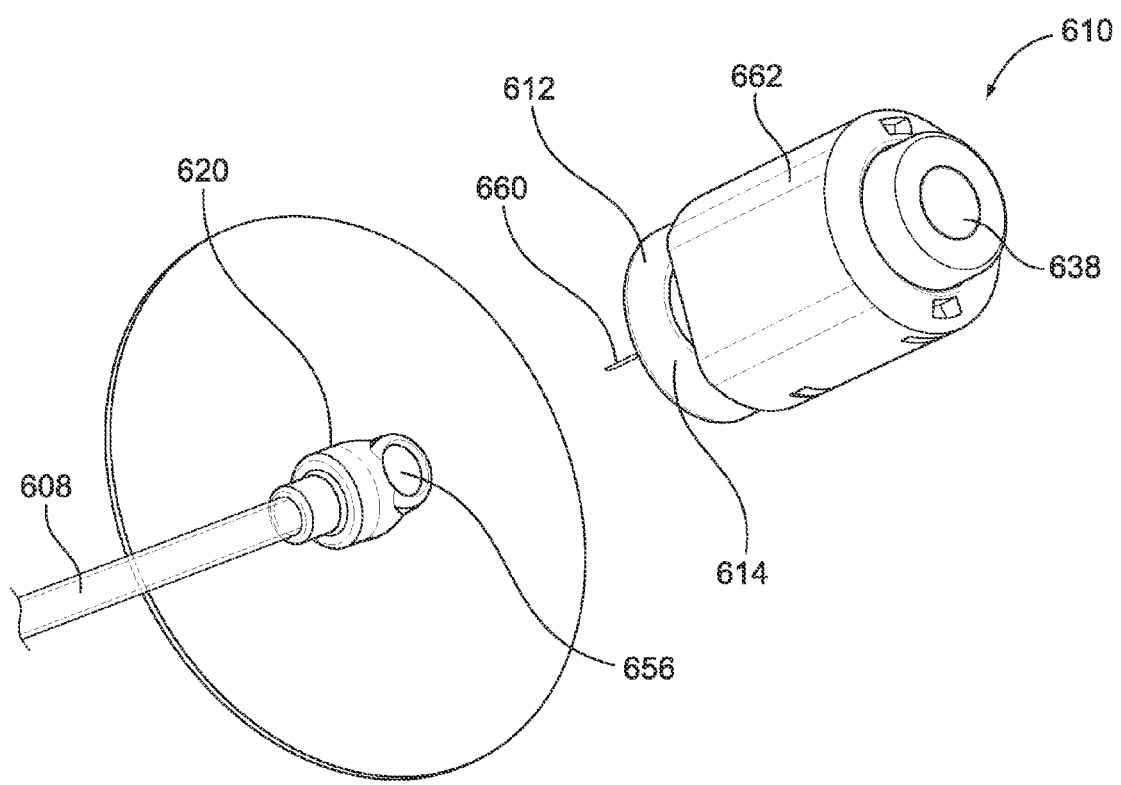
FIG. 6 illustrates another exemplary embodiment of a secondary medicament module that can be used with the infusion pump drug delivery system shown in FIGS. 1 and 2.

FIG. 6 illustrates yet another exemplary embodiment of a secondary medicament module 610. As shown, the secondary medicament module 610 is not permanently incorporated/fixed to the hub 620 of the infusion set. Instead, the hub 620 acts as an injection port for receiving the secondary medicament module 610. As such, the benefits of continuous therapy using the first medicament are maintained while allowing a user to deliver the second medicament 614 without requiring the user to pierce their skin at a separate injection site. This is especially beneficial for users with a phobia of needles and/or dexterity problems.

The hub 620 includes a self-sealing septum 656 that may be made of silicone rubber or a similar elastomeric or self-healing material known in the art. Thus, after a dose of the secondary medicament 614 is delivered and the dispense interface 660 of the secondary medicament module 610 is removed from the septum 658 of the hub 620, the septum 656 re-seals such that contamination of the first medicament flow is prevented. This arrangement allows multiple doses of the same or different secondary medicaments from the same or different secondary medicament modules to be delivered over the life of the infusion set.

The secondary medicament module 610 generally comprises a housing 662, a button 638, a cartridge 612 containing the second medicament 614, and a dispense interface 660. The connection between the hub 620 and the secondary medicament module 610 may be made exclusive. This helps to promote user safety by allowing the hub 620 to interface with specific secondary medicament modules only. However, in other embodiments, the hub 620 may be configured to accept any dispense interface, such as but not limited to a needle of a syringe and/or injection pen known in the art.

In operation, a user inserts the dispense interface 660 of the secondary medicament module 610 into the septum 656 of the hub 620 such that the dispense interface 660 is in fluid communication with the dispense interface (not shown) that is inserted into the skin of the user. The user then activates the secondary medicament module 610 by actuating the button 638. Upon actuation of the button 638 the second medicament 614 is delivered. Although not shown, the secondary medicament module 610 may include a means (e.g., a dial) for setting a user settable dose of the first medicament.

Examples of the present drug delivery system and its various components have been described. Those skilled in the art will understand, however, that changes and modifications may be made to these examples without departing from the true scope and spirit of the present invention, which is defined by the claims.

The invention claimed is:

1. A drug delivery system for delivering at least two medicaments, comprising:
   a pump operably connected to a first reservoir containing a first fluid or medicament;
   a delivery tube, wherein an end of the delivery tube is connected to the first reservoir;
   a dispense interface in fluid communication with the delivery tube; and
   a secondary module in fluid communication with the delivery tube, wherein the secondary module comprises a housing with a bypass channel for delivery of the first fluid or medicament, a second reservoir containing a second fluid or medicament, a proximal needle located at a proximal end of said housing, and a distal needle located at a distal end of said housing,
   wherein the secondary module further comprises an actuation button, wherein the actuation button is configured to permit delivery of the first fluid or medicament when the actuation button is in a non-actuated position, in which the proximal needle and the distal needle are in fluid communication with the bypass channel, and selectively permit delivery of the second fluid or medicament when the actuation button is in an actuated position, in which the proximal needle and the distal needle are in fluid communication with the second reservoir.

2. The drug delivery system of claim 1, wherein the delivery tube is connected to the first reservoir via a hub.

3. A drug delivery system for delivering at least two medicaments, comprising:
   a pump operably connected to a first reservoir containing a first fluid or medicament;
   a delivery tube, wherein an end of the delivery tube is connected to the first reservoir;
   a dispense interface in fluid communication with the delivery tube; and
   a secondary module in fluid communication with the delivery tube, wherein the secondary module comprises (i) a bypass channel for delivery of the first fluid or medicament, (ii) a second reservoir containing a second fluid or medicament, (iii) a proximal needle, (iv) a distal needle, and (v) an actuation button, wherein the actuation button is configured to permit delivery of the first fluid or medicament when the actuation button is in a non-actuated position and selectively permit delivery of the second fluid or medicament when the actuation button is in an actuated position, wherein the actuation button is actuated by sliding the button, the actuation button comprises at least one snap arm configured to engage at least one groove in an inner surface of a housing of the secondary module, the proximal needle is fixed to the actuation button and the at least one groove corresponds to the actuated position of the actuation button.

4. The drug delivery system of claim 3, wherein the at least one groove corresponds to the actuated position of the actuation button.

5. The drug delivery system of claim 4, wherein the secondary module is configured to prevent the actuation button from being reversed to the non-actuated position after actuation.

6. The drug delivery system of claim 1, wherein the secondary module is located near the end of the delivery tube that is connected to the first reservoir.

7. The drug delivery system of claim 1, wherein the secondary module is located at a position between the end of the delivery tube that is connected to the first reservoir and the dispense interface.

8. The drug delivery system of claim 1, wherein the secondary module is located near the dispense interface.

9. The drug delivery system of claim 1, wherein the secondary module in fluid communication with the delivery tube comprises a re-usable secondary module.

10. The drug delivery system of claim 1, wherein the secondary module is releasably coupled to a hub.

11. The drug delivery system of claim 1, wherein the actuation button is actuated by sliding the button, the actuation button comprises at least one snap arm configured to engage at least one groove in an inner surface of a housing of the secondary module, the proximal needle is fixed to the actuation button and the at least one groove corresponds to the actuated position of the actuation button.

12. The drug delivery system of claim 11, wherein the at least one groove corresponds to the actuated position of the actuation button.

13. The drug delivery system of claim 12, wherein the secondary module is configured to prevent the actuation button from being reversed to the non-actuated position after actuation.

* * * * *